United States Patent
Haas (10) Patent No.: US 8,518,383 B2
(45) Date of Patent: Aug. 27, 2013

(54) ORAL CARE PRODUCTS COMPRISING BUFFER SYSTEMS FOR IMPROVED MINERALIZATION/REMINERALIZATION BENEFITS

(75) Inventor: Michael S. Haas, Naperville, IL (US)

(73) Assignee: Wm. Wrigley Jr. Company, Chicago, IL (US)

( * ) Notice: Subject to any disclaimer, the term of this patent is extended or adjusted under 35 U.S.C. 154(b) by 1299 days.

(21) Appl. No.: 11/670,737

(22) Filed: Feb. 2, 2007

(65) Prior Publication Data
US 2008/0050407 A1 Feb. 28, 2008

Related U.S. Application Data

(60) Provisional application No. 60/765,289, filed on Feb. 3, 2006.

(51) Int. Cl.
| | | |
|---|---|---|
| *A61Q 11/00* | (2006.01) |
| *A61K 9/58* | (2006.01) |
| *A61K 8/24* | (2006.01) |
| *A61K 8/19* | (2006.01) |
| *A61K 8/11* | (2006.01) |

(52) U.S. Cl.
USPC ............... 424/57; 424/48; 424/401; 424/602; 424/49; 106/35

(58) Field of Classification Search
USPC ........................................ 424/440
See application file for complete search history.

(56) References Cited

U.S. PATENT DOCUMENTS

| | | |
|---|---|---|
| RE33,161 E | 2/1990 | Chow et al. |
| 5,037,639 A | 8/1991 | Tung |
| 5,268,167 A | 12/1993 | Tung |
| 5,378,131 A | 1/1995 | Greenberg |
| 5,522,893 A | 6/1996 | Chow et al. |
| 5,562,895 A | 10/1996 | Tung |
| 5,571,502 A | 11/1996 | Winston et al. |
| 5,597,554 A | 1/1997 | Wagner |
| 5,603,922 A | 2/1997 | Winston et al. |
| 5,614,175 A | 3/1997 | Winston et al. |
| 5,618,517 A | 4/1997 | Miskewitz |
| 5,645,853 A | 7/1997 | Winston et al. |
| 5,817,296 A | 10/1998 | Winston et al. |
| 5,833,954 A | 11/1998 | Chow et al. |
| 5,858,333 A | 1/1999 | Winston et al. |
| 5,866,102 A | 2/1999 | Winston et al. |
| 5,958,380 A | 9/1999 | Winston et al. |
| 5,980,955 A | 11/1999 | Greenberg et al. |
| 5,993,786 A | 11/1999 | Chow et al. |
| 6,036,944 A | 3/2000 | Winston et al. |
| 6,214,321 B1 * | 4/2001 | Lee et al. .................. 424/52 |
| 6,440,394 B2 | 8/2002 | Barth et al. |
| 6,451,290 B2 | 9/2002 | Winston et al. |
| 6,482,395 B1 | 11/2002 | Barth et al. |
| 6,491,900 B2 | 12/2002 | Chow et al. |
| 6,949,264 B1 | 9/2005 | McGrew et al. |
| 2003/0170185 A1 * | 9/2003 | Takatsuka et al. ........... 424/52 |
| 2005/0260266 A1 * | 11/2005 | Gebreselassie et al. ...... 424/468 |

FOREIGN PATENT DOCUMENTS

WO WO03/059085 7/2003

OTHER PUBLICATIONS

U.S. Appl. No. 60/824,184, filed Aug. 31, 2006.
U.S. Appl. No. 60/765,289, filed Feb. 3, 2006.
U.S. Appl. No. 08/775,088, filed Dec. 30, 1996.
U.S. Appl. No. 08/019,230, filed Feb. 18, 1993.

* cited by examiner

*Primary Examiner* — Frederick Krass
*Assistant Examiner* — Michael P Cohen
(74) *Attorney, Agent, or Firm* — K&L Gates LLP (57) ABSTRACT

Oral products for the improved mineralization/remineralization of teeth are provided. In an embodiment, the present disclosure provides an oral product comprising a calcium salt, a phosphate salt, a sodium salt and a potassium salt. For example, the molar ratio of the sodium salt to the potassium salt ranges from about 3 to about 4.

21 Claims, 1 Drawing Sheet

ORAL CARE PRODUCTS COMPRISING BUFFER SYSTEMS FOR IMPROVED MINERALIZATION/REMINERALIZATION BENEFITS

PRIORITY CLAIM

This application claims the benefit of U.S. Provisional Patent Application Ser. No. 60/765,289 filed on Feb. 3, 2006, the entire disclosure of which is hereby incorporated.

BACKGROUND

The present disclosure generally relates to dental care. More specifically, the present disclosure relates to oral care products for the improved mineralization/remineralization of teeth.

Enamel and dentin in teeth are primarily composed of calcium phosphate in the form of calcium hydroxyapatite. This material is highly insoluble at neutral salivary pH levels, but tends to dissolve in acidic media. Consequently, when teeth are exposed to acids generated during the bacterial-induced glycolysis of carbohydrates, lesions or demineralized areas are initiated below the surface of intact enamel since the outer rim is more acid resistant. Dental caries begin with these subsurface lesions, which are formed before a cavity is even detectable. If not treated, the surface enamel above such a subsurface lesion will eventually collapse, resulting in the formation of a cavity and subsequent loss of tooth structure.

SUMMARY

The present disclosure relates to oral care products for the improved mineralization/remineralization of teeth of a consumer. In an embodiment, the present disclosure provides an oral product comprising a calcium salt, a phosphate salt, a sodium salt and a potassium salt. For example, the molar ratio of the sodium salt to the potassium salt can, in an embodiment, range from about 3 to about 4.

In an embodiment, the oral product releases into the oral cavity of a consumer the calcium salt and the phosphate salt in a molar ratio of about 1.50 to about 1.70.

In an embodiment, the sodium salt and the potassium salt in the oral product can be in a form such as, for example, encapsulated, agglomerated, fixated, entrapped or combinations thereof.

In an embodiment, a polymer used for encapsulation of the sodium salt and potassium salt has a molecular weight of about $1.5 \times 10^3$ g/mol to about $150 \times 10^3$ g/mol.

In an embodiment, a polymer used for encapsulation to salt weight ratio in the oral product is about 10:90 to about 90:10.

In an embodiment, the sodium salt and the potassium salt comprise from about 0.01% to about 80% by total weight of an encapsulation matrix.

In an embodiment, the oral product can be, for example, chewing gums, candies, pressed tablets, mints, chewy candies, hard boiled candies, chocolates, nougats, gels, confectionery pastes, toothpastes, foams, oral rinses, dentifrices or combinations thereof.

In an embodiment, the sodium salt comprises a sodium phosphate compound and the potassium salt comprises a potassium phosphate compound.

In an embodiment, the total amount of the sodium phosphate and the potassium phosphate comprises from about 0.01% to about 10% by weight of the oral product.

In an embodiment, the sodium salt and the potassium salt are kept separately or are not in contact with each other in the oral product until the oral product is consumed, i.e., masticated, dissolved, applied to oral surfaces and the like, alone or in combination.

In an embodiment, the oral product comprises a dual-chambered oral rinse comprising the sodium salt in one chamber and the potassium salt in another chamber.

In an embodiment, the sodium salt and the potassium salt are kept separately in the oral product until the oral product releases the sodium salt and the potassium salt into the mouth of a consumer.

In an embodiment, the calcium salt is triprotic.

In an embodiment, the calcium salt can be, for example, calcium citrate, calcium glycerophosphate or combinations thereof.

In an embodiment, the calcium salt comprises from about 1.0% to about 10.0% by weight of the oral product.

In an embodiment, the oral product can comprise one or more ingredients such as, for example, sweeteners, flavors, colors, sensates, acids, biologically active agents or combinations thereof.

In another embodiment, the present disclosure provides an oral product comprising a calcium salt and encapsulated sodium phosphate and potassium phosphate. The molar ratio of the sodium salt to the potassium salt can range, for example, from about 3 to about 4.

In an embodiment, a blend of the sodium phosphate and the potassium phosphate are encapsulated in a PVAc (e.g. high molecular weight).

In an embodiment, the total amount of the sodium phosphate and the potassium phosphate comprises from about 0.01% to about 10.0% by weight of the oral product.

In an alternative embodiment, the present disclosure provides a chewing gum comprising a calcium salt, a phosphate salt, a sodium salt, and a potassium salt. The molar ratio of the sodium salt to the potassium salt can range, for example, from about 3 to about 4.

In an embodiment, the chewing gum releases the calcium salt and the phosphate salt in a molar ratio of about 1.5 to about 2.0.

In an embodiment, the sodium salt and potassium salt in the chewing gum can be in a form such as, for example, encapsulated, agglomerated, fixated, entrapped or combinations thereof.

In an embodiment, a polymer used for encapsulation of the sodium salt and potassium salt has a molecular weight of about $1.5 \times 10^3$ g/mol to about $150 \times 10^3$ g/mol.

In an embodiment, the polymer to sodium salt and potassium salt weight ratio in the chewing gum is about 10:90 to about 90:10.

In an embodiment, the chewing gum comprises a coating.

In an embodiment, the coating comprises the sodium salt and the potassium salt.

In an embodiment, the chewing gum comprises at least two layers. For example, one layer comprises the calcium salt and another layer comprises the sodium salt and the potassium salt.

In an embodiment, the chewing gum comprises at least three layers. For example, one layer comprises the calcium salt, another layer comprises the sodium salt and another layer comprises the potassium salt.

In an embodiment, the sodium salt comprises a sodium phosphate compound and the potassium salt comprises a potassium phosphate compound.

In an embodiment, a blend of the sodium phosphate compound and the potassium phosphate compound are encapsulated in a PVAc.

In an embodiment, the total amount of the sodium phosphate compound and the potassium phosphate compound comprises about 0.01-10.0% by weight of the chewing gum.

In an embodiment, the calcium salt is selected from the group consisting of calcium citrate, calcium glycerophosphate and combinations thereof.

In an embodiment, the calcium salt comprises from about 1.0% to about 10.0% by weight of the chewing gum.

In an embodiment, the chewing gum comprises one or more ingredients such as, for example, sweeteners, flavors, colors, sensates, acids, biologically active agents and combinations thereof.

In an embodiment, the chewing gum is a sugarless chewing gum.

In still another embodiment, the present disclosure provides a chewing gum comprising a chewing gum shell comprising a calcium salt. The chewing gum shell surrounds a liquid center. The liquid center comprises a sodium salt and a potassium salt. The molar ratio of the sodium salt to the potassium salt can range, for example, from about 3 to about 4.

In an embodiment, the sodium salt comprises a sodium phosphate compound and the potassium salt comprises a potassium phosphate compound.

In an embodiment, the sodium salt and potassium salt in the liquid center comprises a form such as, for example, encapsulated, agglomerated, fixated, entrapped and combinations thereof.

In still another embodiment, the present disclosure provides a method for remineralizing teeth of a consumer. The method comprises providing an oral product comprising a calcium salt, a phosphate salt, a sodium salt and a potassium salt. The molar ratio of the sodium salt to the potassium salt can range, for example, from about 3 to about 4. The oral product is administered into an oral cavity of the consumer.

In an embodiment, the oral product comprises a chewing gum.

In an embodiment, the method further comprises chewing the chewing gum for at least 5 minutes or more.

An advantage of the present disclosure is to provide an improved oral product that provides health benefits.

Another advantage of the present disclosure is to provide an improved oral product capable of mineralizing/remineralizing a consumer's teeth.

Still another advantage of the present disclosure is to provide an improved oral product having a buffering system to assist in mineralizing/remineralizing processes.

Yet another advantage of the present disclosure is to provide an improved chewing gum product capable of mineralizing/remineralizing a consumer's teeth.

Another advantage of the present disclosure is to provide an improved method for mineralizing/remineralizing a consumer's teeth Additional features and advantages are described herein, and will be apparent from, the following Detailed Description and the figures.

DETAILED DESCRIPTION

The present disclosure relates to oral care products for the improved mineralization/remineralization of teeth of consumer. In a general embodiment, the present disclosure provides an oral product comprising a calcium salt, a phosphate salt, a sodium salt and a potassium salt. The molar ratio of the sodium salt to the potassium salt can range be any suitable range such as, for example, from about 3 to about 4. The phosphate salt and the sodium/potassium salt can originate from the same or different compounds.

Stimulated saliva can promote mineralization through the addition of calcium, phosphate and buffer ions. Oral products such as confections and chewing gum can be designed with technologies that offer an effective portable and great tasting means to significantly enhance this baseline salivary mineralization rate. In embodiments, the present disclosures provides oral care products that promote a sustained high level release of ions like calcium, phosphate, sodium and potassium salts for an extended period time in the oral cavity. These ions in turn interact to precipitate amorphous "apatitic-like" calcium-phosphate (CaP) crystals which are sufficient in size to diffuse through a pellicle or plaque layer and lesion surface zone of teeth. Over time, and repeated use, these CaP crystals accumulate and transform to enamel-like structures that reconstitute the subsurface mineral matrix.

It has been surprisingly discovered that the use of a combination sodium and potassium salts in an oral product containing a calcium salt, acts to promote upon placement of this composition in an oral cavity for mastication or consumption, for release and precipitation of the calcium, potassium, and phosphate ions present therein the oral cavity, and thus also acts to promote the subsequent remineralization of the teeth exposed thereto. In particular, this disclosure relates to the use of a sodium salt to potassium salt molar ratio (Na/K) of about 3.0 to about 4.0 in oral products. For example, this ratio is designed to act as a phosphate buffer system to maintain a physiological pH=7.4@37° C., a favorable remineralization environment.

In an embodiment, the total amount of the sodium salt and the potassium salt comprises from about 0.01% to about 10% by weight of the oral product. In another embodiment, the total amount of the sodium salt and the potassium salt comprises from about 6.0% to about 8.0% by weight of the oral product.

Without being held to any particular theory, it is generally believed that, upon initial placement of the product in the oral cavity, calcium, phosphate, sodium and potassium ions are released yielding a Ca/P molar ratio of about 1.50 to about 2.0, preferably from about 1.50 to 1.70. Thus, a precipitate of potassium-substituted amorphous apatite can form, adhere to oral surfaces, and rapidly transform to enamel-like crystal layer. During acid challenge caused by lactic acid from oral plaque bacteria, dissolution of the precipitated potassium-substituted amorphous apatite layer re-establishes favorable remineralization conditions by releasing calcium and phosphate ions near the enamel surface of teeth. Surprisingly, the disclosure offers an opportunity for remineralization without the employment of acids to oral products through its unique buffer system by employing a molar ratio of sodium to potassium of about 3.0 to about 4.0.

In an embodiment, a suitable calcium salt such as, for example, a partially soluble calcium salt such as calcium citrate, is able to deliver a sustained high level of calcium ions from an oral product to the saliva. In another embodiment, a blend of soluble sodium phosphate dibasic and potassium-phosphate monobasic is encapsulated in polyvinylacetate (PVAc) (e.g. high molecular weight) to provide a sustained, high level delivery of phosphate ions ($PO_4$) from gum to the saliva.

The oral products of the present disclosure includes, but are not limited to, chewing gums, candies/confections, gels, toothpastes, foams, oral rinses and/or dentifrices. Compounds that release calcium, phosphate, potassium or sodium ions may be selected from a number of commercially available compounds, and other compounds that are recognized as food additives in other contexts. All such additives encompassed herein are intended to be non-toxic. For the purpose of this disclosure, the term "non-toxic" is intended to conform with accepted and established definitions of safety, such as described by the designation "generally accepted as safe" by the Food and Drug Administration. Also, encompassed in this definition are those compounds that have been added to food for some time and which are recognized as safe under conditions of their intended use. The additives of the disclosure, including calcium salts, are sufficiently non-toxic for oral use at the intended levels on a regular basis, and are preferably stable for a desired shelf life Calcium Salts Although different calcium salts may be employed for mineralization/remineralization of teeth, typical calcium salts include, but are not limited to, the calcium salts of sulfates (e.g., calcium sulfate, anhydrous calcium sulfate, calcium sulfate hemihydrate, calcium sulfate dihydrate), gluconates, (borogluconate), glycerophosphates, polyphosphates, lactates (lactate-gluconate, lactobionate), malates, citrates, tartrates, fumarates, malonates, nitrates, acetates, ascorbates, benzoates, bisulfites, carbonates, chlorides, diglutamates, disodiums, ferrocyanides, formates, fumarates, guanylates, sulfites, hydroxides, inosinates, propionates, peroxides, silicates, sorbates, sulfites, and succinates, as well as calcium oxide, calcium panthothenate, calcium 5'-ribonucleotides and the like, alone or in any combination. The calcium salts employed may be monoprotic, diprotic or triprotic.

Potassium Salts

Although different potassium salts may be employed for mineralization/remineralization of teeth, typical potassium salts include, but are not limited to potassium acetates, potassium adipates, potassium aluminium silicates, potassium ascorbates, potassium benzoates, potassium bicarbonates, potassium bisulfites, potassium bromates, potassium carbonates, potassium chlorides, potassium citrates, potassium ferrocyanides, potassium fumarates, potassium gluconatse potassium hydrogen sulfites, potassium hydroxide, potassium lactates, potassium malates, potassium metabisulfites, potassium nitrates, potassium nitrites, potassium phosphates, potassium propionates, potassium sodium tartrates, potassium sorbates, potassium sulfates, potassium sulfites, potassium tartrates and the like, alone or in combination. The potassium salts employed may be monoprotic, diprotic or triprotic.

Sodium Salts

A variety of sodium salts may be employed for mineralization/remineralization of teeth, typical sodium salts include, but are not limited to sodium acetates, sodium adipates, sodium aluminum phosphates, sodium ascorbates, sodium benzoates, sodium bicarbonates, sodium bisulfites, sodium carbonates, sodium citrates, sodium dehydroacetates, sodium erythorbates, sodium erythorbins, sodium ethyl para-hydroxybenzoates, sodium formates, sodium fumarates, sodium gluconates, sodium hydrogen acetates, sodium chlorides, sodium hydroxides, sodium lactates, sodium malates, sodium metabisulfites, sodium methyl para-hydroxybenzoates, sodium nitrates, sodium nitrites, sodium orthophenyl phenols, sodium propionates, sodium propyl para-hydroxybenzoates, sodium sorbates, sodium stearoyl lactylates, sodium succinates, sodium sulfites, sodium tartrates, sodium tetraborates, soda ash ($Na_2CO_3$), chile saltpeter ($NaNO_3$), monosodium glutamate (MSG), di-, tri-, and tetra-sodium phosphates, and the like, alone or in any combination. The most common source of sodium is sodium chloride, but it occurs in and may be derived from many other minerals such as soda niter, cryolite, amphibole, zeolite, etc. The sodium salts employed may be monoprotic, diprotic or triprotic.

Salt Separation: Encapsulation, Agglomeration Physical & Coatings

In an embodiment, the potassium and sodium salts employed are encapsulated or coated with a barrier layer, in order for example to limit, or substantially prevent the salts from interacting with one or more of the ingredients employed in an oral product. Physical modifications of the potassium and sodium salts by encapsulation with another substrate may increase or delay their release by modifying the solubility or dissolution rates of the salts. For example, the potassium and sodium salts may be coated with silicon dioxide. Still further, the potassium and sodium salts may be encapsulated (e.g. co-encapsulated) together with polyvinylacetate (PVAc). Typically, the amount of PVAc present in the encapsulation matrix is at least about 10% by weight, about 30% by weight, or about 60% by weight or more, the concentration potassium and sodium salts falling within a range of about 0.01% to about 80%, or about 20% to about 70%, or about 30% to about 60% based on the total weight of the encapsulation matrix.

Any standard technique which gives full or partial encapsulation of the salts can be used. These techniques include, but are not limited to, spray drying, spray chilling, fluid-bed coating, extrusion, coextrusion, inclusion, granulation, roll compaction and coacervation. These encapsulation techniques, which give full or partial encapsulation of the salts can be used individually or in combination in a single step process or multiple step process. For example, the salts may be spray-dried, followed by fluid-bed coating of the resultant powder.

The encapsulation techniques of the potassium and sodium salts here described are standard coating techniques and generally give varying degrees of coating, from partial to full coating, depending on the coating composition used in the process. Also, the coating compositions may be susceptible to water permeation of varying degrees. Generally, coating compositions having high organic solubility, good film forming properties and low water solubility give better delayed release of the salts. Such compositions include, but are not limited to, acrylic polymers and copolymers, carboxyvinyl polymer, polyamides, polysterene, polyvinyl acetate, polyvinyl acetate phthalate, polyvinylpyrrolidone and waxes. Although all of these materials may be used for encapsulation of the salts, typically only food-grade materials should be considered.

The polymers used for encapsulation of the sodium phosphate and potassium phosphate salts can have any suitable molecular weight. In an embodiment, the polymer(s) used for encapsulation of the sodium phosphate and potassium phosphate salts have a molecular weight of about $1.5 \times 10^3$ g/mol. The polymer(s) used for encapsulation of the sodium phosphate and potassium phosphate salts can have a molecular weight of about $80 \times 10^3$ g/mol. The polymer(s) used for encapsulation of the sodium phosphate and potassium phosphate salts can also have a molecular weight of about 80 to about $100 \times 10^3$ g/mol. Alternatively, the polymer(s) used for encapsulation of the sodium phosphate and potassium phosphate salts can have a molecular weight of about $150 \times 10^3$ g/mol.

Two standard food-grade coating materials that are good film formers but are not water soluble are shellac and zein.

Others which are more water soluble, but are good film formers are materials like agar, alginates, a wide variety of derivatives like ethyl cellulose, methyl cellulose, sodium hydroxymethyl cellulose, and hydroxypropylcellulose, dextrin, gelatin, starches, and modified starches. These ingredients which are generally approved for food use give a fast release when used as an encapsulant for the salts. In an embodiment, acacia or maltodextrin is used to encapsulate the salts. In still another embodiment, PVAc is used to encapsulate the salts.

The amount of coating or encapsulating material on the salts may also control the length of time of release from oral products. Generally, the higher the level of water-insoluble coating and the lower amount of salts, the slower the release of the salt during mastication. Also, the higher the usage level of a water-soluble coating, the slower the release rate. In an embodiment, to obtain the desired salt release to blend with a oral product's flavor release, the encapsulant is typically a minimum of about 1.0% by weight of the coated salts. For example, the encapsulant is a minimum 1.0% by weight of the encapsulation matrix.

Another method of giving a modified release of the salts is through the process of agglomeration of the salts with an agglomerating agent which partially coats the potassium and sodium salts. This method includes the step of mixing the salt and an agglomerating agent with a small amount of water or solvent. The mixture is prepared in such a way as to have individual wet particles in contact with each other so that a partial coating can be applied. After the water or solvent is removed, the mixture is ground and used as a powdered, coated product.

Materials that can be used as agglomerating agents are the same as those used in encapsulation procedures mentioned previously. However, since the coating is only a partial encapsulation, and the potassium and sodium salts can be slightly water soluble, some agglomerating agents are more effective in modifying the release of the salts than others. Suitable agglomerating agents include, but are not limited to, organic polymers like acrylic polymers and copolymers, polyvinyl acetate (PVAc), polyvinylpyrolidone, waxes, shellac, and zein. Other agglomerating agents include, but are not limited to, agar, alginates, a wide range of cellulose derivatives like ethyl cellulose, methyl cellulose, sodium hydroxymethylcellulose, hydroxypropylmethyl cellulose, dextrin, gelatin, modified and unmodified starches, and vegetable gums like guar gum, locust bean gum, and carrageenan. Even though the agglomerated salts may be only partially coated, when the quantity of the coating is increased compared to the quantity of the salt, the release of the salt can be delayed longer during mastication. In an embodiment, the level of the agglomerating agent is at least 5% by weight of agglomeration matrix.

The potassium salt and sodium salts may be coated together or separately. The salts may be coated in a two-step or multiple step process, either alone or in combination. The salts may be encapsulated with any of the materials described previously and then the encapsulated salts can be agglomerated as described previously to obtain an encapsulated/agglomerated molar ratio of sodium salt to potassium salt, for example, of about 3.5.

In another embodiment, the sodium salt and/or potassium salt may be absorbed onto another component which is porous and becomes entrapped in the matrix of the porous component. Common materials used for absorbing the salts include, but are not limited to, silicas, silicates, pharmasorb clay, spongelike beads or microbeads, amorphous sugars like spray-dried dextrose, sucrose, alditols, amorphous carbonates and hydroxides including aluminum and calcium lakes, vegetable gums and other spray dried materials. Insoluble materials will give the salts a delayed release while water soluble materials will give the salts a fast release from an oral product.

Depending on the type of the absorbent material and how it is prepared, the amount of salts that can be loaded onto the absorbent will vary. Generally, materials like polymers or spongelike beads or microbeads, amorphous sugars and alditols and amorphous carbonates and hydroxides absorb an amount equal to about 10% to about 40% of the weight of the absorbent. Other materials like silicas and pharmasorb clays may be able to absorb about 20% to about 80% of the weight of the absorbent.

The general procedure for absorbing the potassium and/or sodium salt onto an absorbent may be characterized as follows: an absorbent, like fumed silica powder, can be mixed in a powder blender and an aqueous solution of the slightly water soluble salts can be sprayed onto the powder as mixing continues. The aqueous solution can be about 1.0% by weight of the salts and higher solid levels may be used if temperatures of up to 90° C. are used. Generally, water is the solvent, but other solvents like alcohol can also be used if approved for food use. As the powder mixes, the liquid is sprayed onto the powder. Spraying is stopped before the mix becomes damp. The still free flowing powder is removed from the mixer and dried to remove the water or other solvent, then ground to a specific particle size.

After the salt(s) is absorbed onto an absorbent or fixed onto an absorbent, the potassium salt and/or sodium salt can be coated by encapsulation, either or fully or partially, as described elsewhere herein. Alternatively, another form of encapsulation may be used, which is by entrapment of an ingredient by fiber extrusion or fiber spinning into a polymer.

In view of the foregoing, it is to be noted that the four primary methods to obtain a controlled release of the remineralizing/mineralizing agents (e.g. salts) of the present disclosure are (1) encapsulation (either fully or partially), (2) agglomeration, (3) fixation or absorption, and (4) entrapment into a extruded compound. These four methods may be combined in any usable manner which physically modifies the release or dissolvability of the sodium and potassium salts included in this disclosure.

Other methods of treating the sodium salt and/or potassium salt to modify or physically isolate the salts from other ingredients may also have some effect on their release rate, dissolvability or stability. In an embodiment, the potassium salt may be added to one layer of a multi-layered chewing gum composition, and the sodium salt may be added to a different layer of the multi-layered chewing gum composition, and the calcium salt may be added to another different layer of the chewing gum composition.

In yet another embodiment, the potassium and sodium salts may be encapsulated and added to the liquid inside a liquid center oral product. The calcium salt may be added to the material surrounding the liquid center. The center fill of an oral product may comprise one or more carbohydrate syrups, glycerin, thickeners, flavors, acidulants, colors, sweeteners in conventional amounts. The ingredients are combined in a conventional manner. This method of delivery of the sodium, potassium, and calcium salts can allow for a smooth release rate, and can reduce or eliminate possible reactions of the salts prior to consumption thereby enhancing release, improving remineralization/mineralization and yield improved shelf stability.

Another embodiment of isolating the potassium salt and/or sodium salt is to use them in a coating/panning of an oral product. For example, pellet or ball gum is prepared as conventional chewing gum, but formed into pellets that are pillow shaped, or formed into balls. The pellets/balls can then be sugar or polyol coated or panned by conventional techniques to make a unique coated chewing gum. Depending on the salts employed, they can be quite stable and slightly water soluble, making them easy additions to a hot sugar solution for sugar panning. The salts can also be added as a powder blended with other powders often used in some types of panning procedures.

Conventional panning procedures generally coat with sucrose, but recent advances in panning have allowed the use of other carbohydrate materials to be used in the place of sucrose. Some of these components include, but are not limited to, dextrose, maltose, palatinose, xylitol, lactitol, hydrogenated isomaltulose and other alditols, or a combination thereof. These materials may be blended with panning modifiers including, but not limiting to, gum Arabic, maltodextrins, corn syrups, gelatin, cellulose type materials like carboxymethylcellulose (CMC), or hydroxymethylcellulose (HMC), starch and modified starches, vegetable gums like alginates, locust bean gum, gum Arabic, guar gum, and gum tragacanth, insoluble carbonates like calcium carbonate or magnesium carbonate or talc.

Antitack agents may be added as panning modifiers which allow the use of a variety of carbohydrates and sugar alcohols to be used in the development of new panned or coated oral products. For example, the oral products can include, but are not limited to, chewing gums, candies, pressed tablets, mints, chewy candies, hard boiled candies, chocolates, nougats, gels, confectionery pastes, liquids and the like, alone or in any combination. Flavors may also be added with the coating and with the salts of the disclosure to yield unique product characteristics.

In yet another embodiment, another type of coating may be employed to isolate the potassium salt and/or sodium salt from each other and other oral product ingredients. This technique is referred to as a film coating. For example, a film like shellac, Zein, or cellulose-type material is applied onto a product, including but not limiting to chewing gums, candies, pressed tablets, mints, chewy candies, hard boiled candies, chocolates, nougats, gels, confectionery pastes, liquids and the like, alone or in any combination, forming a thin film on the surface of the product. The film may be applied by mixing a polymer, a plasticizer and a solvent (pigments are optional) and spraying the mixture onto surface of another product, coating, or material. This may be accomplished in conventional type panning equipment, or in more advanced side-vented coating pans. When a solvent like alcohol is used, extra precautions are needed to prevent fires and explosions, and specialized equipment is used.

Some film polymers can use water as the solvent in film coating. Recent advances in polymer research and in film coating technology eliminates the problems associated with applying solvents to a coating. These advances make it possible to apply aqueous films to a variety of finished products, including chewing gums, candies, and the like. As the potassium salt and/or sodium salt employed may be slightly water soluble, they can be added to this aqueous film solution and applied with the film to another product surface, coating, or material. The aqueous film, or even the alcohol solvent film, in which the salt or salts may be dispersed may also contain a flavor along with the polymer and plasticizer. By adding the salt or salts to the polymer/plasticizer/solvent system, either as an emulsion or solution, the salt or salts can be added with sweeteners or flavors to balance taste. The potassium salt and/or sodium salt can also be dissolved in the aqueous solvent and coated on the surface with the aqueous film.

Oral Products

The present disclosure is directed to various oral products, including for example chewing gums (e.g., tablet gums, pellet or dragee gums, stick gums, compressed gums, co-extruded layered gums, bubble gums, etc.), candies, confectioneries, chocolates, gels, confectionery pastes, toothpastes, mouth rinses and dentifrices.

In one embodiment, the oral product of the present disclosure is a chewing gum. In another embodiment, the oral product is a co-extruded layered gum, wherein for example the gum comprises one layer which comprises the calcium salt and either: (i) one layer which comprises the co-encapsulated sodium salt and potassium salt having a molar ratio of approximately 3:5 respectively; or, (ii) two layers which comprise the sodium salt in one layer and the potassium salt in another layer having a molar ratio of approximately 3:5. For example, the layer comprising the calcium salt can be present (i.e. sandwiched) therebetween. In this way, the calcium, sodium and potassium salts are essentially encapsulated in the gum base, and thus premature contact of these salts are limited, and likely, substantially prevented.

In another embodiment, chewing gums for delivering the mineralizing/remineralizing components as described herein, are used because the inherent nature of chewing gum allows for prolonged contact with teeth.

Chewing Gums

Chewing gum products of the present disclosure may be made using a variety of different compositions that are typically used in chewing gum compositions. Suitable physical forms include sticks, tabs, dragees, chicklets, batons, and the like. Although exact ingredients for each product form will vary from product to product, the specific techniques will be known by one skilled in the art. In general, a chewing gum composition typically contains a chewable gum base portion which is essentially water-insoluble, and a water-soluble bulk portion which includes water soluble bulking agents and other water soluble components as well as flavors and perhaps other active ingredients which are typically water-insoluble. The water-soluble portion dissipates with a portion of the flavor (and other water insoluble actives, if present) over a period of time during chewing. The gum base portion is retained in the mouth throughout the chew.

The chewing gum may comprise between approximately 5% to about 95% gum base. Typically, the insoluble gum base may comprise between approximately 10% and about 50% of the gum, or from approximately 20% to about 40% of the gum. The present disclosure contemplates employing any commercially acceptable gum base.

The insoluble gum base generally comprises elastomers, elastomer solvents, plasticizers, waxes, emulsifiers, and inorganic fillers. Plastic polymers, such as polyvinyl acetate, which behave somewhat as plasticizers, are also included. Other plastic polymers that may be used include polyvinyl laurate, polyvinyl alcohol, and polyvinyl pyrrolidone. Gum base typically comprises 20 to 40% of the overall chewing gum composition. However, in less common formulations it may comprise as low as 5% or as high as 95%.

Synthetic elastomers may include, but are not limited to, polyisobutylene (e.g. having a weight average molecular weight of about 10,000 to about 95,000), butyl rubber (isobutylene-isoprene copolymer), styrene copolymers (having for example a styrene-butadiene ratio of about 1:3 to about 3:1), polyisoprene, polyethylene, vinyl acetate-vinyl laurate copolymer (having for example a vinyl laurate content of about 5% to about 50% weight of the copolymer), and combinations thereof.

Natural elastomers may include for example natural rubbers such as smoke or liquid latex and guayule, as well as natural gums such as chicle, jelutong, lechi caspi, perillo, sorva, massaranduba balata, massaranduba chocolate, nispero, rosindinha, gutta hang kang and mixtures thereof. Preferred elastomers will depend on, for example, whether the chewing gum in which the base is used is adhesive or conventional, synthetic or natural, bubble gum or regular gum. Elastomers provide the rubbery texture which is characteristic of chewing gum. Elastomers typically make up 5 to 25% by weight of the gum base.

Elastomer solvents which are sometimes referred to as elastomer plasticizers, include but are not limited to natural rosin esters such as glycerol esters, or partially hydrogenated rosin, glycerol esters of polymerized rosin, glycerol esters of partially dimerized rosin, glycerol esters of rosin, pentaerythritol esters of partially hydrogenated rosin, methyl and partially hydrogenated methyl esters of rosin, pentaerthyritol esters of rosin, synthetics such as terpene resins, polylimonene and other polyterpenes and/or any suitable combination of the forgoing. Elastomer solvents are typically employed at levels of 5 to 30% of the gum base.

Gum base plasticizers are sometimes referred to as softeners (but are not to be confused with water soluble softeners used in the water soluble portion of the gum). Typically, these include fats and oils as well as waxes. Fats and oils are typically vegetable oils which are usually partially or fully hydrogenated to increase their melting point. Vegetable oils suitable for such use include oils of cottonseed, soybean, palm (including palm kernal), coconut, shea, castor, peanut, corn, rapeseed, canola, sunflower, cocoa and others. Less commonly used are animal fats such as milk fat, tallow and lard. Structured fats, which are essentially synthetically compounded glycerol esters (triglycerides) of fatty acids of varying chain lengths, offer an ability to carefully adjust the softening profile by use of short and medium chain fatty acids which are less commonly found in nature. Commonly employed waxes include paraffin, microcrystalline and natural waxes such as beeswax and carnauba. Microcrystalline waxes, especially those with a high degree of crystallinity, may be considered bodying agents or textural modifiers. Plasticizers are typically employed at a level of 5 to 40% by weight of the gum base.

Plastic polymers, such as polyvinyl acetate, which behave somewhat as plasticizers, are also commonly used. Other plastic polymers that may be used include polyvinyl laurate, polyvinyl alcohol, and polyvinyl pyrrolidone. Most gum bases incorporate polyvinyl acetate at a level of 5 to 40% by weight of the gum base.

The gum base typically also includes a filler component. The filler component is typically an inorganic powder such as calcium carbonate, ground limestone, magnesium carbonate, talc, silicate types such as aluminum and magnesium silicate, dicalcium phosphate, tricalcium phosphate, cellulose polymers, such as wood, combinations thereof and the like. The filler may constitute from 5% to about 50% of the gum base. Occasionally, a portion of the filler may be added to the chewing gum mixture separately from the gum base.

Emulsifiers, which may also have plasticizing properties, assist in homogenizing and compatibilizing the different base components. Commonly used emulsifiers include mono- and diglycerides such as glycerol monostearate, lecithin, glycerol triacetate, glycerol monostearate, acetylated monoglycerides, fatty acids and combinations thereof. Emulsifiers are commonly used at a level of 1 to 10% by weight of the gum base.

Gum bases commonly contain optional additives such as antioxidants and colors which serve their normal functions. Less commonly, flavors and sweeteners may be added to the gum base. These additives, if used, are typically employed at levels of about 1% or less by weight of the gum base.

The water-soluble portion of the chewing gum may comprise softeners, sweeteners, flavoring agents, and combinations thereof as well as other optional ingredients. For example, the majority of the water soluble portion of the chewing gum will typically comprise a water-soluble, powdered carbohydrate which serves as a bulking agent. In sugar gums, this most often is sucrose although other sugars such as fructose, erythrose, dextrose (glucose), levulose, tagatose, galactose, trehalose, corn syrup solids and the like, alone or in any combination may also be used.

Generally, sugarless chewing gums will employ sugar alcohols (also called alditols, polyols or polyhydric alcohols) as bulking agents due to their benefits of low cariogenicity, reduced caloric content and reduced glycemic values. Such sugar alcohols include sorbitol, mannitol, xylitol, hydrogenated isomaltulose, maltitol, erythritol, hydrogenated starch hydrolysate solids, and the like, alone or in any combination. Longer chain saccharides such as polydextrose and fructo-oligosaccharides are sometimes employed for their reduced caloric properties and other health benefits. The bulking agents typically comprise approximately 5% to about 95% of the gum composition.

Softeners are added to the chewing gum in order to optimize the chewability and mouth feel of the gum. Softeners, also known in the art as plasticizers or plasticizing agents, generally constitute between approximately 0.5% to about 15% of the chewing gum. These include glycerin, propylene glycol and aqueous sweetener solutions (syrups). Examples of syrups include corn syrups and (generically) glucose syrups which are usually prepared from hydrolyzed starch. For sugarless products, the starch hydrolysate may be hydrogenated to produce an ingredient known as hydrogenated starch hydrolysate syrups or maltitol syrups. These HSH syrups have largely replaced sorbitol solutions previously used in sugarless gums because they also function as binders to improve the flexibility and other physical properties of the gum. Softeners are also often used to control the humectancy (water absorbing properties) of the product.

It is often desirable to combine aqueous softeners with glycerin or propylene glycol. One way to accomplish this is through the use of co-evaporated syrups such as those disclosed in U.S. Pat. No. 4,671,961, which is incorporated herein by reference. These syrups provide the benefits of both types of softeners in a single, pumpable liquid with minimal water content.

An emulsifier is sometimes added to the gum to improve the consistency and stability of the gum product. They may also contribute to product softness. Lecithin is the most commonly employed emulsifier, although nonionic emulsifiers such as polyoxyethylene sorbitan fatty acid esters and partial esters of common fatty acids (lauric, palmitic, stearic and oleic acid hexitol anhydrides (hexitans and hexides) derived from sorbitol may also be used. When used, emulsifiers typically comprised 0.5 to 2% of the chewing gum composition.

Suitable surface active agents include surface active agents, which can be salts of potassium, ammonium, or sodium. Sodium salts include anionic surface active agents, such as alkyl sulfates, including sodium lauryl sulfate, sodium laureth sulfate, and the like. Other sodium salts include sodium lauroyl sarcosinate, sodium brasslate, and the like. Suitable ammonium salts include betaine derivatives such as cocamidopropyl betaine, and the like.

In the case of sugarless gums, it is usually desirable to add high intensity sweeteners to compensated for the reduced sweetness resulting from substitution of sugar alcohols for the sucrose in sugar gums. More recently, the trend has been to also add high intensity sweeteners to sugar gums to boost and extend flavor and sweetness. High intensity sweeteners (which are sometimes called high potency or artificial sweeteners) may be defined as food acceptable chemicals which are at least twenty times sweeter than sucrose. Commonly used high intensity sweeteners include aspartame, sucralose, and acesulfame-K. Less common are saccharin, thaumatin, alitame, neotame, cyclamate, perilla derived sweeteners, stevia derived sweeteners, monatin, monellin and chalcones.

Usage levels for high intensity sweeteners may vary widely depending on the potency of the sweetener, local market preferences and the nature and level of other ingredients which might impart bitterness to the gum. Typical levels can range from about 0.01% to about 2%, although some applications may dictate usage outside that range. These sweeteners may be combined together, or with non-high intensity sweeteners at varying levels to impart a sweetness synergy to the overall composition.

Flavors can be employed to impart a characteristic aroma and taste sensation to chewing gum products. Most flavors are water insoluble liquids but water soluble liquids and solids are also known. These flavors may be natural or artificial (synthetic) in origin. Often natural and artificial flavors are combined. It is also common to blend different flavors together in pleasing combinations. Although the range of flavors usable in chewing gums is nearly limitless, they commonly fall into several broad categories. Fruit flavors include lemon, orange, lime, grapefruit, tangerine, strawberry, apple, cherry, raspberry, blackberry, blueberry, banana, pineapple, cantaloupe, muskmelon, watermelon, grape, currant, mango, kiwi and many others as well as combinations. Mint flavors include spearmint, peppermint, wintergreen, basil, corn mint, menthol and others and mixtures thereof. Spice flavors include cinnamon, vanilla, clove, chocolate, nutmeg, coffee, licorice, eucalyptus, ginger, cardamom and many others. Also used are herbal and savory flavors such as popcorn, chili, corn chip and the like. Flavors are typically employed at levels of 0.1 to 4% of the finished gum product. In recent years there has been a trend toward increasing flavor levels to provide higher flavor impact.

It is common to co-dry and encapsulate flavors with various carriers and/or diluents. For example, spray-dried flavors using gum Arabic, starch, cyclodextrin or other carriers are often used in chewing gum for protection, controlled release, control of product texture and easier handling as well as other reasons. When flavors are in such forms, it will often be necessary to increase the usage level to compensate for the presence of the carriers or diluents.

The chewing gum (along with any of the oral products) of the present disclosure may employ various sensates. Generally, sensates may be any compounds that cause a cooling, heating, warming, tingling or numbing, for example, to the mouth or skin. Cooling agents are trigeminal stimulants that impart a cool sensation to the mouth, throat and nasal passages. The most widely known cooling agent is menthol, although this is often considered a flavor due to its aroma properties and the fact that it is a natural component of peppermint oil. More often, the term cooling agent refers to other natural or synthetic chemicals used to impart a cooling sensation with minimal aroma. Commonly employed cooling agents include ethyl p-menthane carboxamide and other N-substituted p-menthane carboxamides, N,2,3-trimethyl-2-isopropyl-butanamide and other acyclic carboxamides, menthyl glutarate (Flavor Extract Manufacturing Association (FEMA 4006)), 3-1-menthoxypropane-1,2-diol, isopulegol, menthyl succinate, menthol propylene glycol carbonate, menthol ethylene glycol carbonate, menthyl lactate, menthyl glutarate, menthone glyceryl ketal, p-menthane-1,8-diol, menthol glyceryl ether, N-tertbutyl-p-menthane-3-carboxamide, p-menthane-3-carboxylic acid glycerol ester, methyl-2-isopryl-bicyclo (2.2.1), heptane-2-carboxamide, menthol methyl ether and others and combinations thereof.

Cooling agents may be employed to enhance the cool taste of mint flavors or to add coolness to fruit and spice flavors. Cooling agents also provide the perception of breath freshening, which is the basis of the marketing of many chewing gums and confections.

Trigeminal stimulants other than cooling agents may be employed in the chewing gums of the present disclosure. These include warming agents such as capsaicin, capsicum oleoresin, red pepper oleoresin, black pepper oleoresin, piperine, ginger oleoresin, gingerol, shoagol, cinnamon oleoresin, cassia oleoresin, cinnamic aldehyde, eugenol, cyclic acetal of vanillin, menthol glycerin ether and unsaturated amides and tingling agents such as Jambu extract, vanillyl alkyl ethers such as vanillyl n-butyl ether, spilanthol, Echinacea extract and Northern Prickly Ash extract. Some of these components are also used as flavoring agents.

Chewing gum generally conveys oral care benefits. In addition to mechanical cleaning of the teeth provided by the chewing action, saliva stimulated by chewing, flavor and taste from the product conveys beneficial properties in reducing bad breath, neutralizing acid, and the like. Saliva also contains beneficial polypeptides and other components which may improve the oral environment. These include: antimicrobial proteins, such as lysozyme, lactoferrin, peroxidases, and histatins; inhibitors of spontaneous crystallization, such as statherin.

The chewing gums of the present disclosure can provide these benefits along with the benefits disclosed herein, and may also be used as vehicles for the delivery of specialized oral care agents. These may include antimicrobial compounds such as Cetylpyridinium Chloride (CPC), triclosan and chlorhexidine; anti-caries agents such as calcium and phosphate ions, plaque removal agents such as abrasives, surfactants and compound/ingredients; plaque neutralization agents such as ammonium salts, urea and other amines; anti-tartar/calculus agents such as soluble pyrophosphates salts; anti halitosis agents such as parsley oil and copper or zinc salts of gluconic acid, lactic acid, acetic acid or citric acid, and whitening agents such as peroxides; agents that may provide either local or systemic anti-inflammatory effects to limit gingivitis, such as COX-2 inhibitors; agents that may reduce dentinal hypersensitivity, such as potassium salts to inhibit nerve cell transmission, and calcium phosphate salts to block the dentinal tubules.

Certain flavors such as peppermint, methyl salicylate, thymol, eucalyptol, cinnamic aldehyde and clove oil (eugenol) may have antimicrobial properties which benefit the oral cavity. These flavors may be present primarily for flavoring purposes or may be added specifically for their antimicrobial properties.

Certain mineral agents may contribute to dental health, in addition to ones disclosed by the disclosure by combating demineralization and enhancing remineralization of teeth. Such ingredients include fluoride salts, dental abrasives and combinations thereof Teeth color modifying substances may be considered among the oral care actives useful. These substances are suitable for modifying the color of the teeth to satisfy the consumer such as those listed in the CTFA Cosmetic Ingredient Handbook, 3rd Edition, Cosmetic and Fragrances Associations Inc., Wash. D.C. (1982), incorporated herein by reference. Specific examples include talc, mica, magnesium carbonate, magnesium silicate, aluminum magnesium carbonate, silica, titanium dioxide, zinc oxide, red iron oxide, brown iron oxide, yellow iron oxide, black iron oxide, ferric ammonium ferrocyanide, manganese violet, ultramarine, nylon powder, polyethylene powder and mixtures thereof.

The chewing gums of the present disclosure may be used to deliver biologically active agents to the chewer. Biologically active agents include vitamins, minerals, anti-oxidants, nutritional supplements, dietary supplements, functional food ingredients (e.g., probiotics, prebiotics, lycopene, phytosterols, stanol/sterol esters, omega-3 fatty acids, adenosine, lutein, zeaxanthin, grape seed extract, ginkgo biloba, isothiocyanates and the like), OTC and prescription pharmaceuticals, vaccines, and nutritional supplements.

It may be desirable to take certain steps to increase or decrease the rate of the release of the agent or to ensure that at least a minimum quantity is released. Such measures as encapsulation, isolation of the active, measures to increase or decrease interaction with the water-insoluble portion of the gum and enteric coating of actives may be employed to that end.

Candies/Confectionaries

As previously discussed, the oral products of the present disclosure may alternatively be in the form of a confectionery product, including for example hard candies, chewy candies, coated chewy center candies, tabletted candies, chocolates, nougats, dragees, confectionery pastes and the like. These candies or confectionery products may comprise any of the various sugars and sweeteners, flavoring agents and/or colorants, as well as other components, known in the art and/or set forth above in the discussion of chewing gums. Additionally, these candies or confectionery products may be prepared using processing conditions and techniques known in the art.

By way of example, a hard candy can be primarily comprised of corn syrup and sugar, and derives its name from the fact that it contains only 1.0% and 4% moisture. In appearance, these types of candies are solid, but they are actually supercooled liquids, which are far below their melting points. There are different types of hard candies. Glass types are usually clear or made opaque with dyes; and grained types, which are always opaque, due to entrapped air and/or moisture.

For illustrative purposes, it is to be noted that a continuous making process for making deposited glass types, with a sugar base can be generally as follows. Sugar corn syrup mixture is spread over a cylinder heated by high pressure steam. Rapid head exchange causes the water in the syrup to evaporate. The cooked syrup is discharged, colors and flavors are added. These can be conveyed directly to hoppers which then discharge directly into molds. The candy is conveyed to batch rollers, which shapes and sizes the batch. The candy enters a former, which shapes the individual pieces into discs, balls, barrels, etc. The present disclosure can be made into any shape, circles, squares, triangles etc, also into animal shapes or any other novelty molding available. The candy is then cooled, wrapped and packaged.

For grained types of candy, water and sugar are the basic components being mixed with other ingredients, and cooked at high temperatures (290° F. 310° F.), causing the water to turn to steam. The product is transferred to a cooling wheel, where it is collected in about 150 pound batches, placed in a pulling machine to aerate the product, and the flavor is added. The candy is transferred to batch rollers where it is shaped and sized. The candy then enters a former, which shapes the individual pieces. The candy is cooled at a relative humidity of 35% and enters a rotating drum where it is coated with a fine sugar. The candy is then conveyed to the graining room for four hours at 90° F. and 60% humidity. The entrapped air and moisture causes the product to grain.

Methods of Mineralization or Remineralization

In general, mineralization or remineralization of a tooth surface may be accomplished by administering an oral product of the disclosure using conditions and techniques known in the art. Regardless of the form of the oral products, it is desirable for its duration in the oral cavity, as well as the rate at which the calcium, potassium, and sodium salts are released from the oral product to be controlled so as to optimize the effectiveness of the product in mineralizing or remineralizing the tooth surface.

For example, in the case of chewing gum, administration typically comprises chewing the gum for at least mi 5 to about 60 minutes, or 10 to about 30 minutes. Generally, a subject is encouraged to chew the gum for a certain period of time for a minimum of about 5 minutes, about 10 minutes, about 15 minutes, about 20 minutes or more.

Without being bound to any particular theory, the inventor of the present disclosure believes that by employing a calcium salt with a molar blend of about 3.0 to about 4.0 of sodium salt and potassium salt offers optimum salt solubility and mineralization/remineralization effects. Further, in oral products that remain in the oral cavity for extended periods of time, this disclosure provides a stability and sustained release of high levels of calcium and phosphate ions over long periods of time. Still further, this disclosure offers mineralization/remineralization effects without the need of incorporating a food acid to stimulate release of the salts from an oral product and into the oral cavity of a consumer for mineralization/remineralization effects.

EXAMPLES

By way of example and not limitation, the following examples are illustrative of various embodiments of the present disclosure and further illustrate experimental testing conducted with the oral care products in accordance with embodiments of the present disclosure, Example Experimental Tests Testing:
The purpose of this test was to evaluate in-vitro efficacy of soluble calcium and phosphate combinations. Testing was conducted at the University of Indiana. Enamel specimens (3×3×3 mm diameter window) were removed from extracted human teeth and mounted on acrylic rods. The enamel surface was ground and polished using alumina slurry, rinsed with deionized water, and air dried. Artificial lesions were then formed in the enamel specimens by a 96 hr immersion in a partially saturated HAP acid buffer consisting of 0.1 mM lactic acid and 0.2 wt % Carbopol C907 adjusted to a pH of 5. Four baseline indentations per specimen were placed with a Vickers diamond at a 200 g load for 15 seconds and the indentation lengths had to be in a range from 25-45 microns. Enamel specimens (N=18 per treatment) were then cycled daily through a series of solutions repeated over an 8 day time period. Artificial saliva, acid challenge and pooled whole saliva solutions were prepared fresh daily. After treatment, the enamel microhardness was assessed and the difference between initial and final microhardness was calculated as a measure of remineralization efficacy. The data was then statistically analyzed with overall treatment comparisons calculated using an ANOVA model at α=0.05. Post ANOVA pairwise comparisons were made using a 2 tailed student t-test.

Treatment Cycle:
Artificial saliva with active treatments (1 hr, 4× daily)

TABLE 1

| Reagents | Quantity Dissolved in 1 L | Molarity |
|---|---|---|
| KCl | 1.114 g | K, Cl: 14.9 mM |
| $CaCl_2 \cdot 2H_2O$ | 0.213 g | Ca: 1.45 mM |
| $KH_2PO_4$ | 0.738 g | $PO_4$: 5.4 mM |
| NaCl | 1.658 g | Na, Cl: 6.5 mM |
| Porcine Muscin (viscosity) | 2.200 g | Ca: P = 0.27[3] and I.S. = 0.058 |

Figure 1:
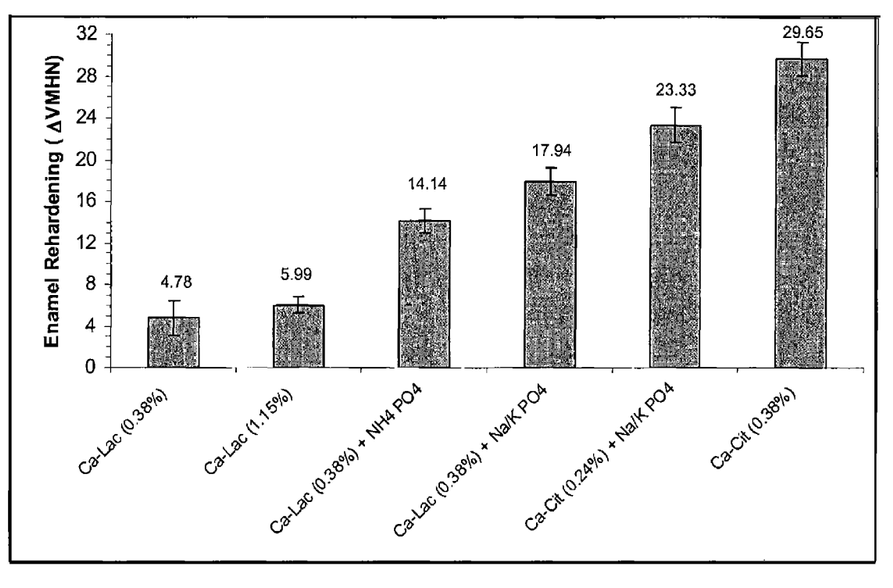
FIG. 1 illustrates In-vitro pH Cycling Screener Results (Calcium-Citrate/Phosphate blend vs. Calcium-lactate) (Mean±SEM, N=18 per group).

Saliva treatment (0.05 ppm fluoride, 30 min daily)
Acid challenge (partially saturated HAP acid/carbopol buffer, Ph 5.0, 20 min., 3× daily)
Saliva film in a humid environment (overnight)
Comparison of Ca-citrate and Ca-citrate+Phosphate blend vs. Ca-lactate (see FIG. 1)

TABLE 2

Treatment groups in Test Series A evaluated by the in-vitro pH cycling model

| Group | | $Ca/PO_4$ ppm | % Salt | Mg/15 ml |
|---|---|---|---|---|
| 1 | Ca Lactate 5-hydrate | 500 | 0.38% | 57.7 |
| 2 | Ca Lactate 5-hydrate | 1500 | 1.15% | 173 |
| 3 | Ca Lactate 5-hydrate $(NH_4)_2HPO_4$ | 500/709 | 0.38% 0.1% | 57.7 14.8 |
| 4 | Ca Lactate 5-hydrate $NH_2HPO_4$ $KH_2PO_4$ | 500/709 | 0.38% 0.1% | 57 11.4 4.4 |
| 5 | Ca Citrate 4-hydrate $NH_2HPO_4$ $KH_2PO_4$ | 500/709 | 0.24% 0.1% | 35.6 11.4 5.7 |
| 6 | Ca Citrate | 811 | 0.38% | 57.7 |

Results

TABLE 3

Statistical Analysis

TTEST Comparisons

| Group A | ΔVSMH | Group B | ΔVSMH | p(2-tail) |
|---|---|---|---|---|
| CaLac (500) | 4.78 | CaLac (1500) | 5.99 | NS |
| CaLac (500, 0.38%) | 4.78 | CaCit (811, 0.38%) | 29.55 | 1.3E−08 |
| CaLac (500) | 4.78 | CaLac (500) + Di(NH4)PO4 (709) | 14.16 | 1.0E−04 |
| CaLac (500) | 4.78 | CaLac (500) + Na/KPO4 (709) | 17.94 | 7.1E−06 |
| CaLac (1500) | 5.99 | CaLac (500) + Di(NH4)PO4 (709) | 14.16 | 2.4E−06 |
| CaLac (1500) | 5.99 | CaLac (500) + Na/KPO4 (709) | 17.94 | 1.2E−06 |
| CaLac (500) + Di(NH4)PO4 (709) | 14.16 | CaLac (500) + Na/KPO4 (709) | 17.94 | 0.04 |
| CaLac (500) + Na/KPO4 (709) | 17.94 | CaCit (500) + Na/KPO4 (709) | 23.33 | 0.002 |
| CaLac (500) + Na/KPO4 (709) | 17.94 | CaCit (811) | 29.65 | 6.6E−05 |
| CaCit (500) + Na/KPO4 (709) | 23.33 | CaCit (811) | 29.65 | 0.0091 |

Based on the data provided, one can make the following observations:

No significant dose response was observed with Ca-lactate at 500 and 1500 ppm respectively.

The addition of phosphate salts (709 ppm) to a Ca-lactate (500 ppm) solutions provided significantly higher enamel rehardening over Ca-lactate alone (500 and 1500 ppm respectively). This indicated that phosphate addition was a key driver for remineralization.

A molar blend of Na/K phosphate salts provided higher enamel rehardening over diammonium phosphate salts at equal phosphate ion concentration. This indicated that Na/K phosphate molar blend may be a better pH buffer over the ammonium ion.

At equivalent calcium and phosphate ion concentrations, solutions with the citrate anion provided higher enamel rehardening over the lactate anion. It is hypothesized the triprotic citrate anion could potentially provide a mineralization/remineralization template through simultaneous adsorption to the tooth surface and sequestering of Ca ions. The lactate anion though is monoprotic and may not provide this templating effect.

At equivalent mass percent (0.38%) in solution, Ca-citrate (21% Ca) provided higher enamel rehardening over Ca-lactate (13% Ca) through the addition of higher concentrations of Ca ions. This indicated that greater calcium addition was a key driver for mineralization/remineralization.

Example

Oral Care Product Formulations

TABLE 4

| Chewing Gum Compositions: | | | | | | | |
|---|---|---|---|---|---|---|---|
| Ingredients (Weight %) | Ex. 1 | Ex. 2 | Ex. 3 | Ex. 4 | Ex. 5 | Ex. 6 | Ex. 7 |
| Gum Base | 33.23 | 30.60 | 31.10 | 35.60 | 35.1 | 34.23 | 31.87 |
| Sorbitol | 41.12 | 39.00 | 35.00 | 35.50 | 35.1 | 42.72 | 41.00 |
| Calcium citrate | 6.75 | 7.50 | 10.00 | 8.50 | 4.50 | * | 3.34 |
| Calcium glycerophosphate | * | * | * | * | * | 7.75 | 3.34 |
| Encapsulated sodium phosphate (47%) and potassium phosphate (13%) | 5.00 | 7.50 | 10.00 | * | * | 6.00 | 7.00 |
| Encapsulated sodium phosphate (35%) and potassium phosphate (15%) | * | * | * | 6.00 | 12.00 | * | * |
| Calcium carbonate | 7.00 | 7.00 | 7.00 | 7.00 | 5.00 | 4.00 | 8.50 |
| Glycerin | 4.00 | 5.50 | 4.00 | 4.50 | 5.00 | 3.00 | 2.50 |
| Encapsulated sweetener | 0.75 | 0.75 | 0.75 | 0.75 | 0.25 | 1.00 | 1.25 |
| Flavor | 1.30 | 1.30 | 1.30 | 1.30 | 1.50 | 1.00 | 1.00 |
| Menthol | 0.45 | 0.45 | 0.45 | 0.45 | 0.75 | * | * |
| Color | 0.15 | 0.15 | 0.15 | 0.15 | 0.05 | 0.15 | 0.15 |
| WS-23 | 0.15 | 0.15 | 0.15 | 0.15 | 0.50 | * | * |
| High intensity sweetener | 0.10 | 0.10 | 0.10 | 0.10 | 0.25 | 0.15 | 0.05 |
| Total Weight % | 100% | 100% | 100% | 100% | 100% | 100% | 100% |

TABLE 5

| Chewing Gum Compositions: | | | | | | |
|---|---|---|---|---|---|---|
| Ingredients (Weight %) | Ex. 8 | Ex. 9 | Ex. 10 | Ex. 11 | Ex. 12 | Ex. 13 |
| Sugar | 50.50 | 32.30 | * | * | * | * |
| Xylitol | * | 32.30 | 63.60 | * | * | * |
| Sorbitol | * | * | * | 63.60 | 40.90 | 20.00 |
| Mannitol | * | * | * | * | 12.00 | 25.00 |
| Gum Base | 19.20 | 19.20 | 19.60 | 19.60 | 25.50 | 30.00 |
| Corn syrup | 15.90 | 1.40 | * | * | * | * |
| Glycerin | 1.40 | 12.90 | 12.90 | 12.90 | 5.60 | 8.00 |
| Cooling Agent | 0.20 | * | * | * | * | 0.50 |
| Flavor | 0.80 | 0.90 | 0.90 | 0.90 | 1.00 | 1.50 |
| Encapsulated sodium phosphate (47%) and potassium phosphate (13%) | * | * | * | * | * | 7.50 |
| Encapsulated Sodium Phosphate | 3.00 | * | 3.00 | * | 4.00 | * |
| Encapsulated Potassium Phosphate | 3.00 | * | * | 3.00 | 4.00 | * |
| Encapsulated Calcium citrate | * | * | * | * | 7.00 | * |
| Calcium Citrate | 6.00 | 6.00 | * | * | * | 7.50 |
| Total Weight % | 100% | 100% | 100% | 100% | 100% | 100% |

TABLE 6

| Coating Compositions | | | | | | |
|---|---|---|---|---|---|---|
| Ingredients (Weight %) | Ex. 14 | Ex. 15 | Ex. 16 | Ex. 17 | Ex. 18 | Ex. 19 |
| Xylitol | 90.00 | 90.00 | 87.74 | * | * | * |
| Maltitol | * | * | * | 80.10 | 74.70 | 67.2 |
| Maltitol Powder | * | * | * | 10.00 | 15.00 | 20.00 |
| Gum Arabic | 4.00 | 5.00 | 7.00 | 8.50 | 7.50 | 9.00 |
| Flavor | 0.50 | 0.50 | 0.66 | 0.70 | 0.90 | 0.5 |
| Titanium Dioxide | 0.50 | 0.84 | — | 0.50 | 0.50 | 0.5 |
| Talc | 0.10 | 0.10 | 0.10 | 0.10 | 0.10 | 0.2 |
| Wax | 0.10 | 0.10 | 0.10 | 0.10 | 0.10 | 0.2 |
| Color | * | * | 1.40 | * | 0.20 | 0.40 |
| Encapsulated sodium phosphate (47%) and potassium phosphate (13%) | 4.80 | * | * | * | * | * |
| Encapsulated Sodium Phosphate | * | * | 3.00 | * | * | * |
| Encapsulated Potassium Phosphate | * | * | * | 3.00 | * | * |
| Encapsulated Calcium citrate | * | * | * | * | 1.00 | * |
| Sodium Phosphate | * | * | * | * | * | 2.00 |
| Calcium Citrate | * | 4.00 | * | * | * | * |
| Total Dry Weight % | 100% | 100% | 100% | 100% | 100% | 100% |

TABLE 7

Hard Candy Compositions

| Ingredients (Weight %) | Ex. 20 | Ex. 21 | Ex. 22 | Ex. 23 | Ex. 24 |
|---|---|---|---|---|---|
| Corn Syrup | 37.00 | * | * | 45.3 | * |
| Sugar | 46.50 | * | * | 45.0 | * |
| Polyalcohol | * | 86.30 | 80.00 | * | 92.8 |
| Flavor | 1.00 | 3.00 | 2.00 | 5.0 | 3.5 |
| Color | 0.50 | 0.50 | 1.00 | 0.5 | 0.4 |
| Encapsulated sodium and potassium phosphate (50% sodium phosphate and 10% potassium phosphate) | 7.50 | 5.00 | 8.50 | * | 3.00 |
| Calcium Citrate | 7.50 | 5.00 | 8.50 | 4.00 | * |
| High Intensity Sweetener | * | 0.20 | * | 0.20 | 0.3 |
| Total Dry Weight % | 100% | 100% | 100% | 100% | 100% |

TABLE 8

Pressed Mint Compositions

| Ingredients (Weight %) | EX. 25 | EX. 26 | EX. 27 | EX. 28 | EX. 29 |
|---|---|---|---|---|---|
| Sorbitol | 82.85 | 93.85 | 87.85 | 96.85 | 94.85 |
| Flavor | 1.00 | 1.00 | 1.00 | 1.00 | 1.00 |
| Mg Stearate | 0.95 | 0.95 | 0.95 | 0.95 | 0.95 |
| High Intensity Sweetener | 0.20 | 0.20 | 0.20 | 0.20 | 0.20 |
| Encapsulated sodium and potassium phosphate (50% sodium phosphate and 10% potassium phosphate) | 7.50 | 2.00 | 5.00 | * | 1.00 |
| Calcium Citrate | 7.50 | 2.00 | 5.00 | 1.00 | 2.00 |
| Total Dry Weight % | 100% | 100% | 100% | 100% | 100% |

TABLE 9

Oral Rinse Composition

| Ingredients (Weight %) | Ex. 30 | Ex. 31 | Ex. 32 |
|---|---|---|---|
| Calcium citrate | 10.00 | * | * |
| Sodium phosphate and potassium phosphate in a molar ratio of 3:4 | * | 8.00 | * |
| Chlorhexidene gluconate | * | * | 0.12% |
| Ethanol | 11.60 | 11.60 | 11.60 |
| Sodium saccharin | 0.15 | 0.15 | 0.15 |
| FD&C Blue No. 1 | 0.001 | 0.001 | 0.001 |
| Peppermint oil | 0.50 | 0.50 | 0.50 |
| Glycerin | 10.00 | 10.00 | 10.00 |
| Tween | 50.00 | 50.00 | 50.00 |
| Water | 17.74 | 19.74 | 27.63 |
| Total Weight % | 100% | 100% | 100% |

Example 33: Examples 30 and 31 are kept in separate chambers of an oral mouthrinse composition and upon dispensing the mouthrinse they are released into the oral cavity of a consumer simultaneously.

Example 34: Examples 30, 31 and 32 are kept in separate chambers of an oral mouthrinse composition and upon dispensing the mouthrinse they are released into the oral cavity of a consumer simultaneously.

Example 35: Example 30 is used a liquid center in a multilayered chewing gum composition with the chewing gum of Example 4 and the coating composition of Example 15.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. An oral product comprising:
   calcium citrate; and
   a sodium phosphate salt and a potassium phosphate salt, wherein the phosphate salts are encapsulated together in a molar ratio of sodium phosphate salt to potassium phosphate salt ranging from about 3 to about 4, and wherein the oral product releases the calcium citrate and the phosphate salts in a molar ratio of about 1.5 to about 2.0.

2. The oral product of claim 1, wherein the sodium phosphate salt and the potassium phosphate salt are encapsulated in a polyvinyl acetate, the polyvinyl acetate to phosphate salts weight ratio in the oral product being from about 10:90 to about 90:10.

3. The oral product of claim 1, wherein the total amount of the sodium phosphate salt and the potassium phosphate salt comprises from about 0.01% to about 10.0% by weight of the oral product.

4. The oral product of claim 1, wherein the oral product is selected from the group consisting of pressed tablets, chewy candies, hard boiled candies, mints, chocolates, nougats, gels and confectionary pastes.

5. A chewing gum comprising:
   calcium citrate;
   a sodium phosphate salt; and
   a potassium phosphate salt, wherein the molar ratio of the sodium phosphate salt to the potassium phosphate salt ranges from about 3 to about 4, and wherein the chewing gum releases the calcium citrate and the phosphate salts in a molar ratio of about 1.5 to about 2.0.

6. The chewing gum of claim 5, wherein the sodium phosphate salt and potassium phosphate salt comprise a form selected from the group consisting of encapsulated, agglomerated, fixated, entrapped and combinations thereof.

7. The chewing gum of claim 5, comprising a polymer that encapsulates the sodium phosphate salt and potassium phosphate salt having a molecular weight of about $1.5 \times 10^3$ g/mol to about $150 \times 10^3$ g/mol.

8. The chewing gum of claim 7, wherein the polymer to phosphate salts weight ratio in the chewing gum is about 10:90 to about 90:10.

9. The chewing gum of claim 5, wherein the chewing gum comprises a coating.

10. The chewing gum of claim 9, wherein the coating comprises the sodium phosphate salt and the potassium phosphate salt.

11. The chewing gum of claim 5, wherein the chewing gum comprises at least two layers, wherein one layer comprises the calcium salt and another layer comprises the sodium phosphate salt and the potassium phosphate salt.

12. The chewing gum of claim 5, wherein the chewing gum comprises at least three layers, wherein one layer comprises the calcium salt, another layer comprises the sodium phosphate salt and another layer comprises the potassium phosphate salt.

13. The chewing gum of claim 5, wherein a blend of the sodium phosphate compound and the potassium phosphate compound are encapsulated in a polyvinyl acetate.

14. The chewing gum of claim 5, wherein the total amount of the sodium phosphate compound and the potassium phosphate compound comprises about 0.01-10.0% by weight of the chewing gum.

15. The chewing gum of claim 5, wherein the calcium salt comprises from about 1.0% to about 10.0% by weight of the chewing gum.

16. The chewing gum of claim 5, wherein the chewing gum is a sugarless chewing gum.

17. A chewing gum comprising:
a chewing gum shell, the chewing gum shell comprising calcium citrate; and
a liquid center surrounded by the chewing gum shell, the liquid center comprising a sodium phosphate salt and a potassium phosphate salt, wherein the molar ratio of the sodium phosphate salt to the potassium phosphate salt ranges from about 3 to about 4, and wherein the chewing gum releases the calcium citrate and the phosphate salts in a molar ratio of about 1.5 to about 2.0.

18. The chewing gum of claim 17, wherein the sodium phosphate salt and potassium salt phosphate comprise a foam selected from the group consisting of encapsulated, agglomerated, fixated, entrapped and combinations thereof.

19. A method for remineralizing teeth of a consumer, the method comprising:
providing an oral product comprising calcium citrate, a sodium phosphate salt and a potassium phosphate salt, wherein the molar ratio of the sodium phosphate salt to the potassium phosphate salt ranges from about 3 to about 4, and wherein the oral product releases the calcium citrate and the phosphate salts in a molar ratio of about 1.5 to about 2.0; and
administering the oral product into an oral cavity of the consumer.

20. The method of claim 19, wherein the oral product comprises a chewing gum.

21. The method of claim 20, wherein the method further comprises chewing the chewing gum for at least 5 minutes.

* * * * *